US011668707B2

(12) United States Patent
Brunelle (10) Patent No.: US 11,668,707 B2
(45) Date of Patent: Jun. 6, 2023

(54) SIMULTANEOUS MEASUREMENT OF MULTIPLE ANALYTES OF A LIQUID ASSAY

(71) Applicant: Siemens Healthcare Diagnostics Inc., Tarrytown, NY (US)

(72) Inventor: Jacques Brunelle, Franklin, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 262 days.

(21) Appl. No.: 16/468,963

(22) PCT Filed: Dec. 12, 2017

(86) PCT No.: PCT/US2017/065737
§ 371 (c)(1),
(2) Date: Jun. 12, 2019

(87) PCT Pub. No.: WO2018/111829
PCT Pub. Date: Jun. 21, 2018

(65) Prior Publication Data
US 2020/0080994 A1 Mar. 12, 2020

Related U.S. Application Data

(60) Provisional application No. 62/435,353, filed on Dec. 16, 2016.

(51) Int. Cl.
*G01N 33/536* (2006.01)
*G01N 21/27* (2006.01)
(Continued)

(52) U.S. Cl.
CPC ......... *G01N 33/536* (2013.01); *G01N 21/272* (2013.01); *G01N 21/3151* (2013.01);
(Continued)

(58) Field of Classification Search
CPC ............... G01N 33/536; G01N 21/272; G01N 21/3151; G01N 21/77; G01N 33/721;
(Continued)

(56) References Cited

U.S. PATENT DOCUMENTS 5,882,935 A * 3/1999 Hirai .................... G01N 33/723
436/67
7,283,242 B2 10/2007 Thornton
(Continued)

FOREIGN PATENT DOCUMENTS

DE 3633916 A1 4/1988
JP S50010678 A1 2/1975
(Continued)

OTHER PUBLICATIONS

Brown et al., "Matrix Representations and Criteria for Selecting Analytical Wavelengths for Multicomponent Spectroscopic Analysis", 1982, Anal. Chem., 54, 1472-1479 (Year: 1982).*
(Continued)

*Primary Examiner* — Jill A Warden
*Assistant Examiner* — Henry H Nguyen (57) ABSTRACT

Analyzers and methods for making and using analyzers are described such as a method in which multiple absorption readings of a liquid assay are obtained by a photodetector using multiple light sources having at least three separate and independent wavelength ranges and with each of the absorption readings taken at a separate instant of time. Using at least one processor and calibration information of the liquid assay, an amount of at least two analytes within the liquid assay using the multiple absorption readings is determined.

15 Claims, 8 Drawing Sheets

US 11,668,707 B2
Page 2

(51) Int. Cl.
| | |
|---|---|
| G01N 21/31 | (2006.01) |
| G01N 21/77 | (2006.01) |
| G01N 33/72 | (2006.01) |
| G01N 35/10 | (2006.01) |
| G01N 21/82 | (2006.01) |
| G01J 3/10 | (2006.01) |
| G01J 3/00 | (2006.01) |
| G01N 33/70 | (2006.01) |
| G01N 33/68 | (2006.01) |
| G01J 3/42 | (2006.01) |

(52) U.S. Cl.
CPC ........... G01N 21/77 (2013.01); G01N 33/721 (2013.01); G01N 35/1002 (2013.01); *B01L 2300/0663* (2013.01); *G01J 3/00* (2013.01); *G01J 3/10* (2013.01); *G01J 3/42* (2013.01); *G01N 21/82* (2013.01); *G01N 33/6827* (2013.01); *G01N 33/70* (2013.01); *G01N 33/726* (2013.01); *G01N 2021/3129* (2013.01); *G01N 2021/3148* (2013.01); *G01N 2021/825* (2013.01); *G01N 2201/061* (2013.01)

(58) Field of Classification Search
CPC ......... G01N 35/1002; G01N 2201/061; G01N 33/70; G01N 33/726; G01N 33/6827; G01N 2021/825; G01N 21/82; G01N 2021/3129; G01N 2021/3148; B01L 2300/0663; G01J 3/10; G01J 3/00; G01J 3/42

See application file for complete search history.

(56) References Cited

U.S. PATENT DOCUMENTS

| | | | |
|---|---|---|---|
| 9,289,764 B2 | 3/2016 | Lange et al. | |
| 2003/0186449 A1 | 10/2003 | Yonehara et al. | |
| 2006/0234263 A1 | 10/2006 | Light, II | |
| 2007/0222973 A1 | 9/2007 | Hoshiko et al. | |
| 2008/0234560 A1* | 9/2008 | Nomoto | A61B 5/14552 600/310 |
| 2009/0181413 A1* | 7/2009 | Itoh | C12Q 1/60 435/11 |
| 2012/0077282 A1* | 3/2012 | Katzlinger | G01J 3/0291 422/67 |
| 2013/0171028 A1 | 7/2013 | Shaffer et al. | |
| 2013/0171675 A1* | 7/2013 | Tsukamoto | G01N 21/8483 435/14 |
| 2014/0017814 A1* | 1/2014 | Tanaka | G01N 33/543 436/501 |
| 2014/0192342 A1* | 7/2014 | Sass | G01N 21/31 356/40 |
| 2015/0105295 A1 | 4/2015 | Kiesel et al. | |
| 2015/0132789 A1* | 5/2015 | Bornheimer | G01N 21/6428 435/29 |

FOREIGN PATENT DOCUMENTS

| | | |
|---|---|---|
| JP | S51009491 A1 | 1/1976 |
| JP | H08159954 A | 6/1996 |
| JP | H09274041 A | 10/1997 |
| JP | 2005253478 A | 9/2005 |
| JP | 2010187604 A * | 9/2010 |
| JP | 2012247188 A | 12/2012 |
| JP | 2013076713 A | 4/2013 |
| JP | 2014500509 A | 1/2014 |
| JP | 5554000 B2 | 7/2014 |
| JP | 2014521095 A | 8/2014 |
| JP | 2015062681 A | 4/2015 |
| JP | 2015515006 A | 5/2015 |
| JP | 2016540974 A | 12/2016 |
| WO | 2009016811 A1 | 2/2009 |
| WO | 2013046861 A1 | 4/2013 |
| WO | 2015005257 A | 1/2015 |
| WO | 2015073384 A1 | 5/2015 |

OTHER PUBLICATIONS

Translation of JP2010187604A, Noshio, Tomohisa, Sep. 2, 2010 (Year: 2010).*
Translation of JP2005253478A, Egawa, Shunji, Sep. 22, 2005 (Year: 2005).*
European Search Report and Search Opinion of European Application No. 17881988.4 dated Sep. 26, 2019.
Vucic et al., "An Automated Immunoturbidimetric Assay for HbA1c Determination", 1998, Clinical Chemistry and Laboratory Medicine: CCLM, pp. 1-8.
International Search Report and Written Opinion of International Application No. PCT/US2017/065737 dated Feb. 15, 2018.

* cited by examiner

SIMULTANEOUS MEASUREMENT OF MULTIPLE ANALYTES OF A LIQUID ASSAY

This application claims priority to U.S. Provisional Application No. 62/435,353, filed Dec. 16, 2016, the disclosure of which is hereby incorporated by reference in its entirety.

FIELD OF THE INVENTION

The presently disclosed and claimed inventive concept(s) relate to an analyzer that monitors and/or reads a liquid assay using at least two separate and independent wavelength ranges.

BACKGROUND OF THE INVENTION

Various types of analytical tests related to patient diagnosis and therapy can be performed by analysis of a liquid sample taken from a patient's infections, bodily fluids or abscesses. Such devices have been proven to be effective in diagnostic assays that detect the presence and quantity of certain analytes indicative of a patient's health, including, but not limited to, hemoglobin, glycated hemoglobin (HbA1c), microalbumin and creatinine, and lipid-based analytes, such as cholesterol, triglycerides, and/or high-density lipoproteins. These assays are typically conducted with automated clinical analyzers onto which tubes or vials containing patient samples have been loaded. The analyzer extracts a liquid sample from the vial and combines the sample with various reagents in special reaction cuvettes or tubes. Point of care analyzers are also used to analyze the liquid samples. Point of care analyzers are typically located at a physician's office and permit the physician and/or the physician's staff to immediately obtain and analyze the liquid sample. In point of care analyzers, the liquid samples are normally manually loaded into a cartridge which is placed within the point of care analyzer and then analyzed.

With respect to automated clinical analyzers, usually the sample-reagent solution is incubated or otherwise processed before being analyzed.

With automated clinical analyzers and point of care analyzers, analytical measurements are often performed using a beam of interrogating radiation interacting with the sample-reagent combination to generate turbidimetric, fluorometric, absorption readings or the like. The readings allow determination of end-point or rate values from which an amount of analyte related to the health of the patient may be determined using well-known calibration techniques. As mentioned above, such optical inspection machines provide individual doctors, nurses and other caregivers with powerful medical diagnostic tools.

An analyzer used in a point of care location has been sold by Siemens Healthcare Diagnostics under the trade name DCA VANTAGE. This analyzer analyzed assays with light confined to a single wavelength of 531 nm. This analyzer also detected Hb and HbA1c in a sequential fashion. Other analyzers use 2 or 3 wavelengths in a sequential measurement, one wavelength is used to determine Hb, a second wavelength is used to determine HbA1c (still subtracting Hb from (Hb+HbA1c)) and a third wavelength (if present) was used to apply a correction for interfering substances (e.g. lipid, bilirubin). In this analyzer, the first and second wavelengths were selected so that the absorbance at the second wavelength in the assay due to Hb was zero.

It has been found that the time for reading multiple analytes from a samples, however, could be improved. It is to such an improved analyzer that reads multiple analytes of interest in a shortened amount of time that the present disclosure is directed.

SUMMARY

In some embodiments, an analyzer is described. In these embodiments, the analyzer is provided with a housing, a first light source, a second light source, a third light source, a sample detector, and a computer system. The housing surrounds a test cartridge space sized and is configured to receive a test cartridge containing a liquid test sample—reagent mixture configured to undergo an immunotype reaction. The first light source generates a first beam of light passing through the test cartridge space, the first beam of light having a first wavelength range. The second light source generates a second beam of light passing through the test cartridge space, the second beam of light having a second wavelength range different from the first wavelength range. The third light source generates a third beam of light passing through the test cartridge space. The third beam of light as a third wavelength range different from the first and second wavelength ranges. The at least one sample detector is positioned to receive one or more of the first, second and third beams of light subsequent to the first, second and third beams of light passing through the test cartridge space to generate first, second and third signals. The computer system has a processor configured to receive the first, second, and third signals indicative of light captured by the sample detector at first, second and third instants of time and to use the first, second and third signals with calibration data to determine an amount of at least two analytes of interest simultaneously within the liquid test sample-reagent mixture.

In some embodiments, multiple absorption readings of a liquid assay undergoing an immunotype reaction are obtained by at least one photodetector using multiple beams of light having at least three separate and independent wavelength ranges and with at least two of the absorption readings taken at a separate instant of time and within an absorption curve of a first analyte within the liquid assay. Using at least one processor, an algorithm solves for the amounts of the first analyte and a second analyte in multiple simultaneous equations, and calibration information of the liquid assay, an amount of the first analyte and the second analyte within the liquid assay using the multiple absorption readings is determined.

In some embodiments, at least one light source configured to generate at least three separate and independent wavelength ranges are mounted within a light source space such that light beams generated by the at least one light source pass within a test cartridge space sized and dimensioned to receive a test cartridge containing a liquid assay. At least one sample photodetector is mounted in a sample detector space such that the at least one sample photodetector is configured to receive at least a portion of the light beams after the light beams pass within the test cartridge space. In these embodiments, the at least one light source and the at least one sample photodetector is coupled to a main processor having computer executable logic that when executed by the main processor cause the main processor to obtain at least three absorption readings at separate and independent wavelength ranges during an immunotype reaction of the liquid assay by the sample photodetector and with each of the absorption readings taken at a separate instant of time, and determine an amount of at least two analytes within the liquid assay using calibration information of the liquid assay, the multiple absorption readings and an algorithm that solves for the amounts of the at least two analytes in multiple simultaneous equations.

BRIEF DESCRIPTION OF THE DRAWINGS

A more complete appreciation of the present disclosure and many of the attendant advantages thereof will be readily understood by reference to the following detailed description when taken in conjunction with the accompanying drawings, in which.

DESCRIPTION OF THE PREFERRED EMBODIMENTS

Before explaining at least one embodiment of the inventive concept(s) in detail by way of exemplary drawings, and laboratory procedures, it is to be understood that the inventive concept(s) is not limited in its application to the details of construction and the arrangement of the components set forth in the following description or illustrated in the drawings. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the devices and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a processor" may refer to 1 or more, 2 or more, 3 or more, 4 or more or greater numbers of processors. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the liquid test sample utilized in accordance with the presently disclosed and claimed inventive concept(s) is from about 1 to about 100 microliters. As used herein, the term "volume" as it relates to the liquid test sample utilized in accordance with the presently disclosed and claimed inventive concept(s) means from about 0.1 microliter to about 90 microliters, or from about 1 microliter to about 75 microliters, or from about 2 microliters to about 60 microliters, or less than or equal to about 50 microliters.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "light" refers to electromagnetic radiation having a wavelength within the electromagnetic spectrum, including wavelengths within a visible portion of the electromagnetic spectrum and wavelengths outside of the visible portion of the electromagnetic spectrum.

Turning now to particular embodiments, the presently disclosed and claimed inventive concept(s) relate to a device (s), kit(s), and method(s) for reading a liquid assay, i.e., a liquid test sample—reagent mixture undergoing an immunotype reaction. More specifically, the presently disclosed and claimed inventive concept(s) relate to an analyzer that monitors and/or reads a liquid assay using at least three separate and independent wavelength ranges.

Figure 1:
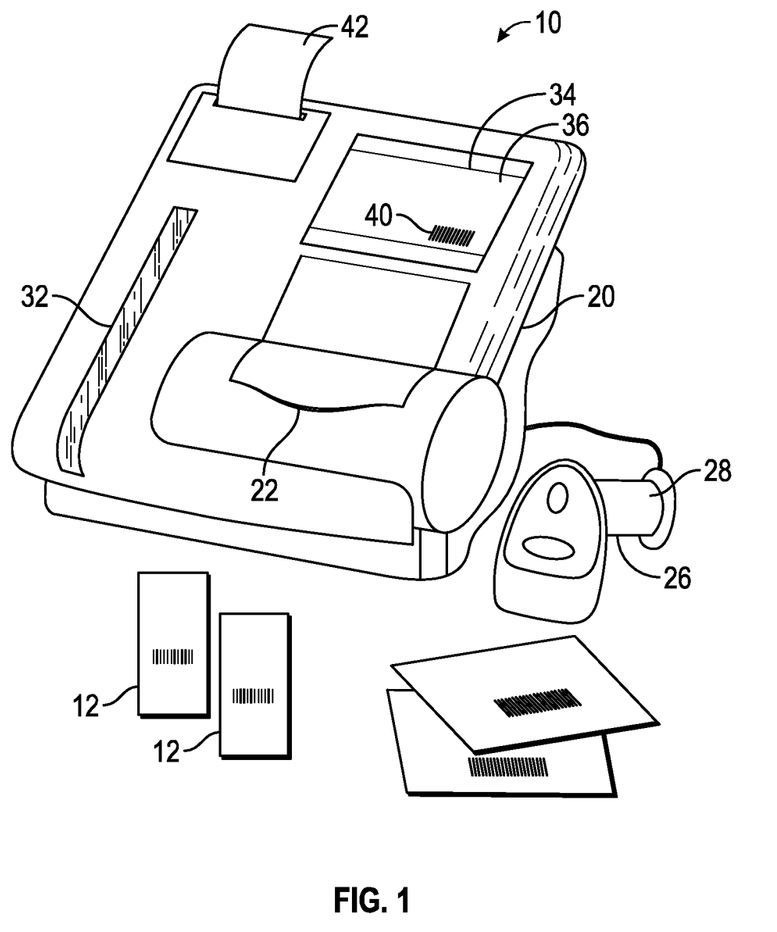
FIG. 1 is a perspective view of an exemplary point of care analyzer constructed in accordance with the present disclosure for more accurately measuring the amount of one or more analytes of interest within a sample.

Referring now to FIG. 1, shown therein and designated by a reference numeral 10 is one embodiment of an analyzer constructed in accordance with the presently disclosed inventive concepts. In some embodiments, the analyzer 10 is a computer-controlled spectrophotometer designed to perform measurements with single-use reagent test cartridges 12 (two of which are shown in FIG. 1 by way of example and referred to hereinafter as a "test cartridge") that can be used to analyze a liquid test sample for two or more analytes of interest. The analyzer 10 is also provided with a cartridge holder 16 (see FIG. 5) designed to temporarily receive one or more of the test cartridges 12 and support the one or more test cartridges 12 while the liquid test sample within the test cartridge 12 is being analyzed. In some embodiments, the analyzer 10 is configured to work with a reagent cartridge for measuring $HbA1_c$ as a percent of total hemoglobin (tHb) in blood.

Hemoglobin A1c is formed by a non-enzymatic glycation of the N-terminus of the ß-chain of hemoglobin Ao. The level of hemoglobin $A1_c$ is proportional to the level of glucose in the blood over a period of approximately two months. Thus, hemoglobin $A1_c$ is accepted as an indicator of the mean daily blood glucose concentration over the preceding two months. Studies have shown that the clinical values obtained through regular measurement of hemoglobin A1c lead to changes in diabetes treatment and improvement of metabolic control as indicated by a lowering of hemoglobin A1c values. To measure the percent concentration of hemoglobin A1c in blood, both the concentration of hemoglobin A1c specifically and the concentration of total hemoglobin are measured, and the ratio reported as percent hemoglobin A1c. All of the reagents and materials for determining the concentration of hemoglobin A1c and total hemoglobin may be contained within one of the test cartridges 12.

The analyzer 10 is provided with a housing 20 having an optics door 22 that is openable to provide access to a test cartridge space 24 (see FIG. 6) within the housing 20, and closable so as to block exterior light and prevent unwanted light interference within the test cartridge space 24. In one embodiment, the test cartridge space 24 is sized and dimensioned to receive one of the test cartridges 12 supported by the cartridge holder 16.

The analyzer 10 may also be provided with one or more readers 26 configured to scan an identification code on the test cartridge 12. The identification code can be implemented in a variety of manners such as a QR code, or a barcode. In the example shown, the analyzer 10 is provided with a portable reader 28, and a fixed reader 30. The housing 20 may be shaped to form a slot 32 sized and dimensioned to receive at least a portion of the test cartridge 12. The fixed reader 30 can be positioned in a variety of locations on or in the housing 20. For example, the fixed reader 30 can be positioned adjacent to the slot 32 so as to read the identification code on the test cartridge 12 as the test cartridge 12 is swiped through the slot 32. Or, the fixed reader 30 can be positioned adjacent to the optics door 22 to read the identification code on the test cartridge 12 as the test cartridge 12 is being inserted onto the cartridge holder 16.

Before the liquid test sample can be analyzed, the identification code on the test cartridge 12 may be scanned. The identification code may be indicative of a lot number and a test name. The information obtained from the identification code may be used to access appropriate calibration parameter values (calibration curve) for a particular lot number of reagent test cartridges in use. If no calibration curve is stored or accessible by the analyzer 10 for the particular lot number of test cartridges 12 in use, the analyzer 10 may prompt the user to scan a calibration card containing an appropriate calibration curve. In some embodiments, appropriate calibration parameter values can be encoded into the identification code and read when the identification code is scanned by the portable reader 28 and/or the fixed reader 30.

The analyzer 10 may also be provided with a user interface 34 permitting a user to interact with, control and receive information from the analyzer 10. For example, once amounts of at least two analytes of interest within the liquid test sample-reagent mixture are determined, such amounts can be reported to the user using the user interface 34 and then a health care professional can render a procedure or other health care to the patient according to the amounts reported to the user. The user interface 34 can be implemented in a variety of manners, such as a graphical display 36, a speaker 38, a touch screen 40, a printer 42 and combinations thereof.

Figure 2:
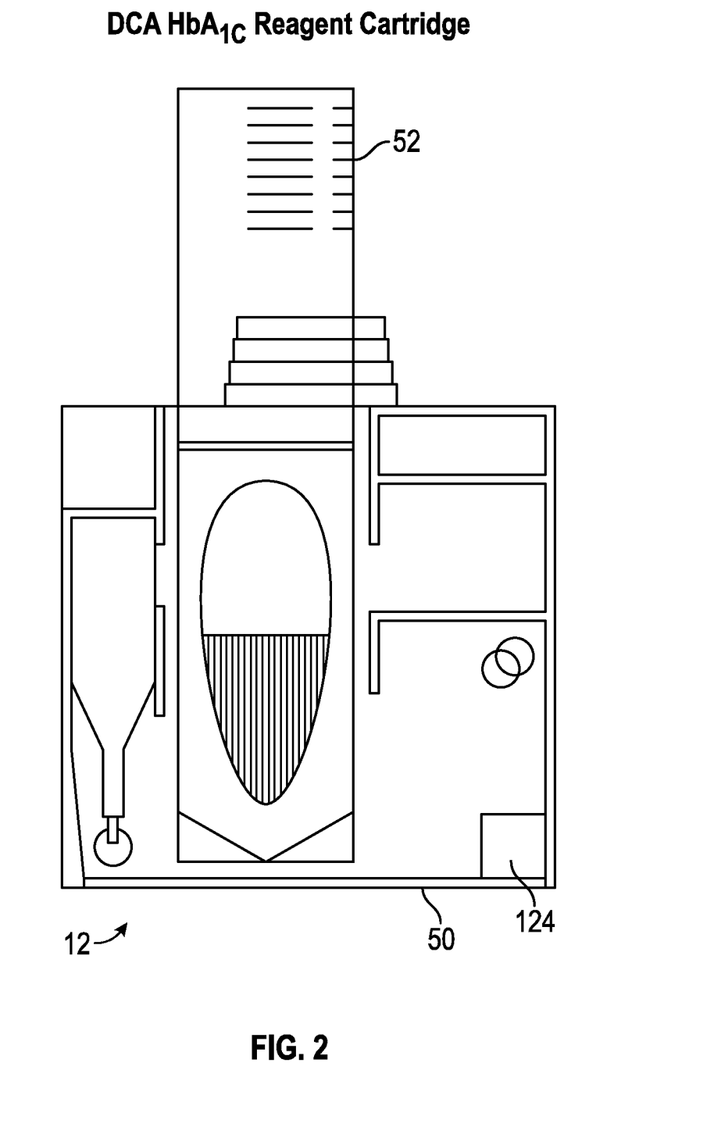
FIG. 2 is a side elevational view of an exemplary test cartridge for use with the point of care analyzer depicted in FIG. 1.

Shown in FIG. 2 is an exemplary test cartridge 12. Suitable test cartridges 12 are commercially available and known to those skilled in the art. In general, each test cartridge 12 includes a housing 50 defining a fluidic circuit (not shown) containing, for example, at least two reagents, a buffer solution, an aggulutinator, an antibody latex, an oxidant, a tab 52, at least one mixing/reaction chamber, and at least one fluidic path connecting the components of the fluidic circuit together. The agglutinator (e.g., a synthetic polymer containing multiple copies of the immunoreactive portion of HbA1c) causes agglutination of latex coated with HbA1c specific mouse monoclonal antibody. This agglutination reaction causes increased scattering of light, which is measured as an increase in absorbance. The buffer can be a clear, colorless, aqueous matrix in which chemical reactions take place during liquid test sample measurements. The tab 52 isolates the buffer solution within the housing 50 from the fluidic path. In use, an operator introduces a liquid test sample into the test cartridge 12. The operator then inserts the test cartridge 12 into the cartridge holder 16 and pulls the tab 52 to release the buffer solution before starting the measurement. After the measurement sequence starts, the analyzer 10 may selectively rotate the test cartridge 12 to mix reagent, buffer, and liquid test sample at various reaction steps. The analyzer 10 may also selectively rotate the test cartridge 12 into various positions for optical measurements.

Figure 3:
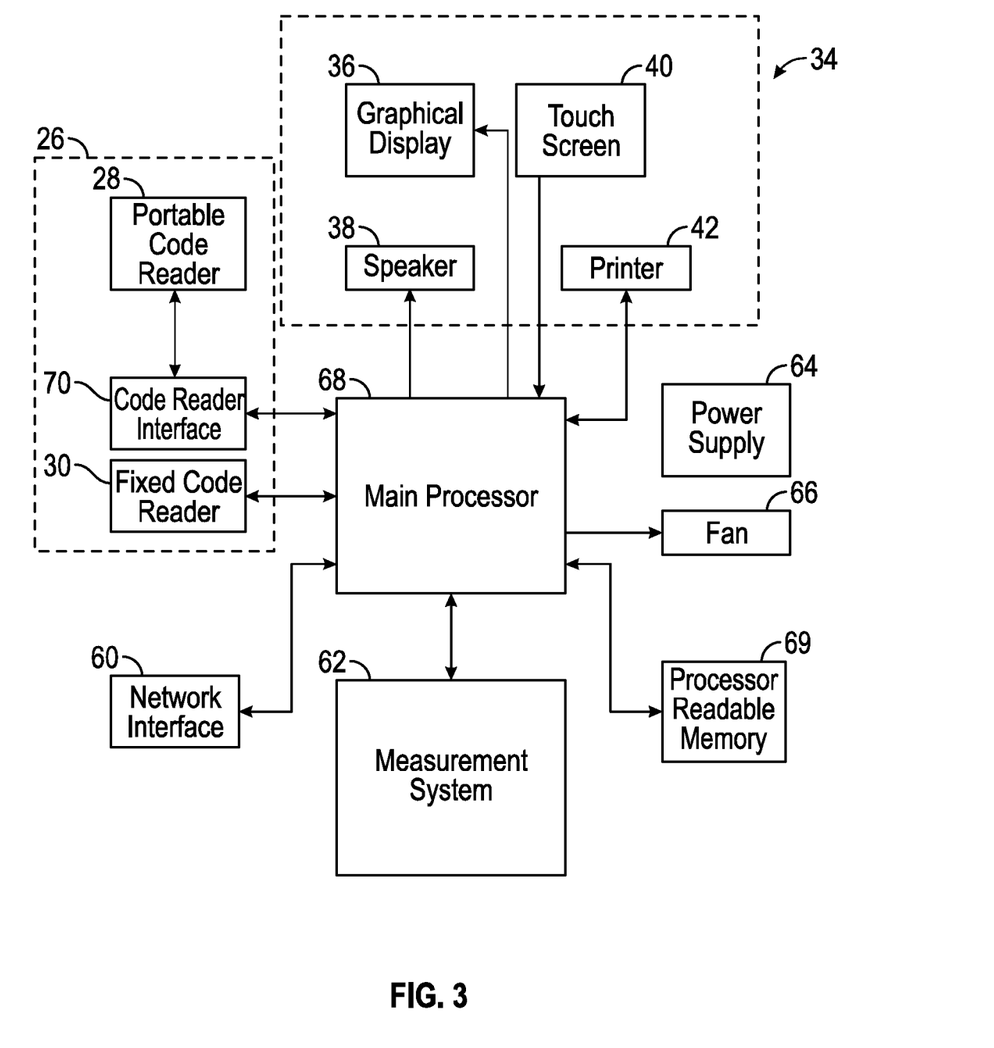
FIG. 3 is a block diagram of one embodiment of the analyzer of FIG. 1.

Shown in FIG. 3 is a block diagram of the analyzer 10. In general, the analyzer 10 includes the reader(s) 26, the user interface 34, a network interface 60, a measurement system 62, a power supply 64, a fan 66, a main processor 68 communicating with the reader 26, the user interface 34, the network interface 60, the measurement system 62, and the fan 66 via any suitable communication path, such as a bus, and a processor-readable memory 69 storing instructions to cause the main processor 68 to perform the functions described herein. When the fixed reader 30 is remote from the optics door 22 and/or the cartridge holder 16, once the identification code on the test cartridge 12 has been scanned, the test cartridge 12 is placed into the test cartridge space 24, the optics door 22 is closed, and the user interface 34 is utilized to actuate the measurement system 62 into conducting a measurement of the liquid test sample within the test cartridge 12. When the fixed reader 30 is positioned adjacent to the cartridge holder 16, the identification code on the test cartridge 12 is scanned when the test cartridge 12 is placed into the test cartridge space 24 of the cartridge holder 16.

The network interface 60 can be designed to communicate with any suitable type of network, such as an Ethernet network and can be a wireless interface or a wired interface. The network interface 60 can be configured to communicate with one or more predetermined external servers or computers, such as a predetermined data manager using any suitable protocol, such as a POCT1-A2 communication protocol configured to simplify connectivity to data managers such as RAPIDComm Data Management System. The main processor 68 can be programmed to automatically upload test results to an LIS/HIS or other data manager via the network interface 60. Further, the processor-readable memory 69 may include sufficient onboard memory to store historical test results, such as up to 4,000 test results and 1,000 operator names.

The power supply 64 can be any suitable type of power supply which is capable of regulating and supplying appropriate power to the various components within the analyzer 10. For example, the power supply 64 can be a switching power supply and/or a battery-powered, or solar powered power supply. The fan 66 circulates air within the housing 20 so as to selectively cool the various components within the housing 20. The housing 20 may be formed from plastic, composite, metal, or any other suitable material that may be opaque to light within the visible spectrum to reduce optical interference during testing.

The reader 26 can be provided with a code reader interface 70, such as a serial port or a USB port, designed to interface the portable reader 28 to the main processor 68 via any suitable communication path.

Figure 4:
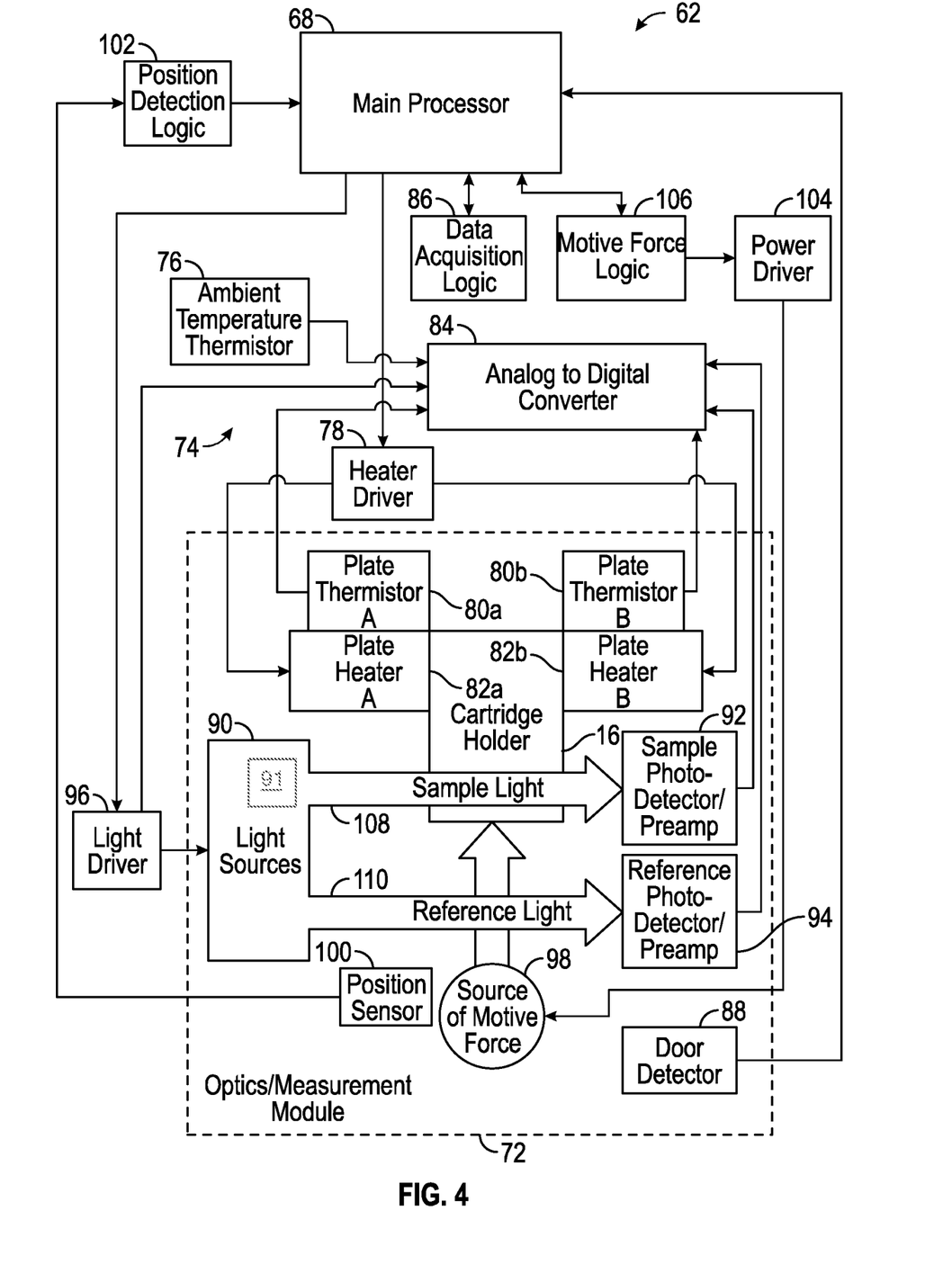
FIG. 4 is a block diagram of an exemplary measurement system of the analyzer of FIGS. 1 and 3.

Shown in FIG. 4 is a block diagram of an exemplary embodiment of the measurement system 62 constructed in accordance with the present disclosure. In general, the measurement system 62 is provided with a measurement module 72, and an environmental module 74. The measurement module 72 is configured to execute a test sequence and thereby conduct multiple readings from the test cartridge 12. The environmental module 74 is configured to control various environmental parameters, such as temperature, and ambient light surrounding the test cartridge 12 so as to provide a stable, predictable environment thereby eliminating various noise and/or inaccuracies which may be present due to changes in the environmental parameters. In the example shown, the environmental module 74 is provided with an ambient temperature thermistor 76, a heater driver 78 one or more plate thermistors 80 (two plate thermistors 80a and 80b being shown in FIG. 4 by way of example), one or more heater plates 82 (two heater plates 82a and 82b being shown in FIG. 4 by way of example). The plate thermistors 80a and 80b are designed to measure a temperature of the test cartridge 12 and supply signals indicative of the temperature of the test cartridge 12 to the main processor 68 via an analog-to-digital converter 84, and data acquisition logic 86. The heater plates 82a, and 82b are configured to receive power from the heater driver 78 and thereby supply energy into the test cartridge 12 for regulating the temperature of the test cartridge 12. The ambient temperature thermistor 76 measures ambient temperature surrounding the test cartridge 12 and supplies signals indicative of the ambient temperature to the main processor 68 via the analog-to-digital converter 84 and the data acquisition logic 86. The main processor 68 receives the information supplied by the ambient temperature thermistor 76 and the plate thermistors 80a and 80b, and uses such information to regulate the temperature of the test cartridge 12 by supplying control signals to the heater driver 78.

In the example shown, the cartridge holder 16 has two heater plates 82a and 82b (heater elements) in contact with the test cartridge 12. Each heater plate 82a and 82b has a respective one of the plate thermistors 80a and 80b in thermal contact with the heater plates 82a and 82b, and the voltage to each heater plate 82a and 82b may be controlled independently. A Proportional-Integral-Derivative (PID) algorithm may be used to control temperature of the heater plates 82a and 82b. In this example, there is no temperature sensor in the test cartridge 12. Therefore, in this example, this is a closed-loop system in regard to the temperature of the heater plates 82a and 82b, but an opened-loop system in regard to the temperature of the liquid test sample in the test cartridge 12. The temperature measured by each plate thermistor 80a or 80b may be computed using formulas and algorithms known to those skilled in the art The environmental module 74 may also be provided with an optics door detector 88, e.g., a switch, for determining whether or not the optics door 22 is in an open or closed position. Ideally, the optics door 22 is constructed of an optically opaque material and sealed with the housing 20 when closed so as to eliminate unwanted light within the test cartridge space 24. If a test sequence is run when the optics door 22 is open, then the test results resulting from the test sequence may be discarded.

The measurement module 72 is provided with multiple light sources 90 (or a single light source having the ability to output light at multiple distinct wavelength ranges, or multiple mixed wavelength ranges (e.g., white light) as discussed below), one or more sample photodetector(s) 92, one or more reference photodetector(s) 94, a light driver 96, a source of motive force 98, a position sensor 100, position detection logic 102, a power driver 104 and motive force logic 106. When the light source 90 generates light including multiple mixed wavelength ranges, the light source 90 may also include a separator 91, such as a prism or grating to separate the mixed wavelength ranges into distinct wavelength ranges and provide the distinct wavelength ranges to the one or more sample photodetector(s) 92, one or more reference photodetector(s) 94, e.g., using a system of light valves (not shown). When a single light source 90 is used, the sample photodetector 92 can be implemented as (a) a single photodetector that is agnostic to wavelengths of light within a predefined range of wavelengths, or (b) multiple wavelength selective photodetectors.

The measurement module will be described hereinafter, by way of example, as having the multiple light sources 90, a single reference photodetector 94, and a single sample photodetector 92. The multiple light sources 90 are positioned adjacent to the test cartridge space 24 to selectively illuminate the test cartridge 12 and obtain transmittance readings from the test cartridge 12 at at least three distinct wavelength bands of light. The light emitted by the light sources 90 are split into a sample beam 108 passing through an optical window 124 of the test cartridge 12, and a reference beam 110 avoiding the test cartridge 12. The light of the sample beam 108 is received by the sample photodetector 92 and converted into a sample signal indicative of the transmittance of the light of the sample beam 108. The light of the reference beam 110 is received by the reference photodetector 94 and converted into a reference signal indicative of the transmittance of the light outside of the test cartridge 12. Power is supplied to the multiple light sources 90 via the light driver 96 and the particular one of the multiple light sources 90 selected for emission at any particular instance of time may be controlled by the main processor 68 providing control signal(s) to the light driver 96.

The source of motive force 98 may be controlled by the main processor 68 via the motive force logic 106 and the power driver 104. In one embodiment, the source of motive force 98 can be a stepper motor, and in this instance, the motive force logic 106 can be stepper motor driver logic, and the power driver 104 can be a stepper motor driver circuit. The main processor 68 monitors and controls the position of the test cartridge 12 via position detection logic 102 communicating with the position sensor 100. The position sensor 100 directly or indirectly detects a real-time position of the test cartridge 12 and generates a signal indicative of the real-time position of the test cartridge 12. The signal indicative of the real-time position of the test cartridge 12 is supplied to the position detection logic 102 which interprets the signal to generate control information and then passes the control information to the main processor 68.

Figure 5:
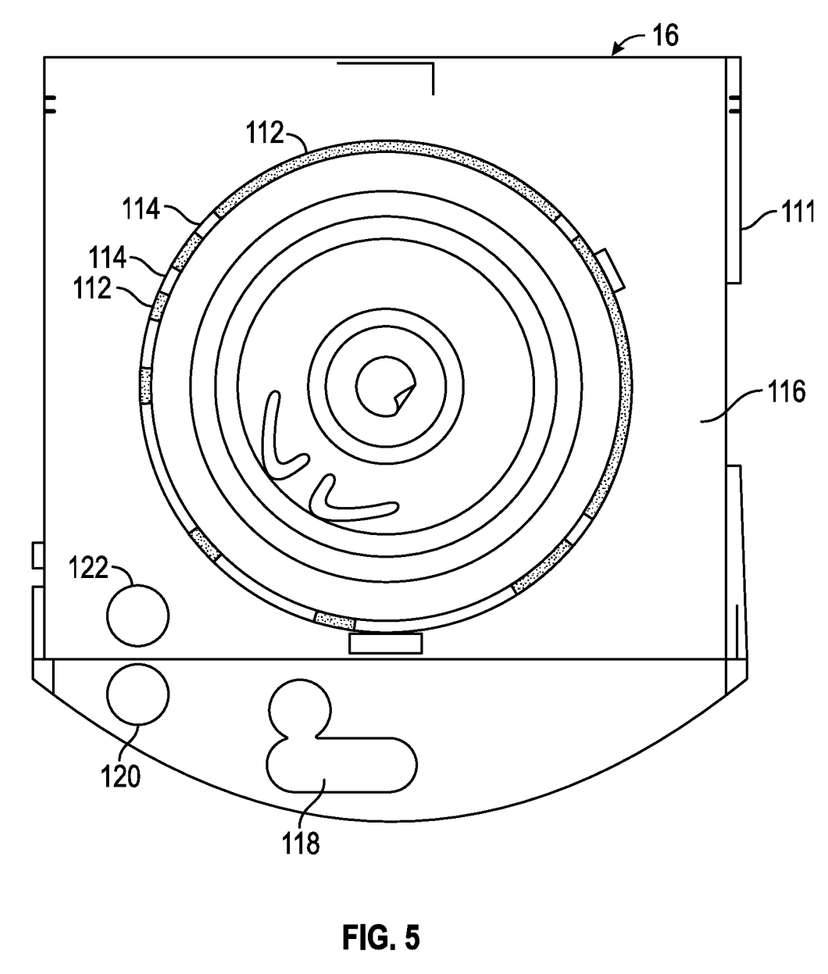
FIG. 5 is a top plan view of an exemplary cartridge holder for holding and supporting the test cartridge of FIG. 2 within the analyzer depicted in FIG. 1.

A top plan view of the exemplary cartridge holder 16 is shown in FIG. 5. The cartridge holder 16 is designed to mate with and support the test cartridge 12 while permitting the test cartridge 12 to be read. In this example, the cartridge holder 16 is provided with a support member 111 having a pattern of posts 112 and slots 114 to provide information to the position sensor 100 as to the current position of the cartridge holder 16. The pattern of posts 112 and slots 114 can be molded into and extend from a surface 116 of the support member 111 that faces the source of motive force 98. As the cartridge holder 16 rotates, the posts 112 and slots 114 alternately block and pass light emitted from the position sensor 100. As the cartridge holder 16 rotates, several rotational angles can be determined by counting the blocked-to-clear and clear-to-blocked transitions. This enables the main processor 68 to understand how to control the source of motive force 98 so as to accurately position the cartridge holder 16. The support member 111 of the cartridge holder 16 is provided with a home air read aperture 118, a reference air read aperture 120, and a sample read aperture 122. The home air read aperture 118, the reference air read aperture 120, and the sample read aperture 122 can be designed with a variety of shapes and sizes to selectively pass or block the sample beam 108 and the reference beam 110 as described hereinafter. When the cartridge holder 16 is rotated into a Home/Air Read position (e.g., motor step +8), the sample beam 108 passes through an upper, circular part of the home air read aperture 118 and the reference beam 110 passes through the lower, elongated part of the home air read aperture 118. In a Sample Read position (e.g., motor step +25), the sample beam 108 passes through the sample read aperture 122 and through the optical window 124 (located in the lower corner of the test cartridge 12 as shown in FIG. 2). The reference beam 110 passes through the reference air read aperture 120 and underneath the test cartridge 12. In a Dark Read position, both the sample beam 108 and the reference beam 110 fall between the apertures 118, 120 and 122 and are blocked by the support member 111 of the cartridge holder 16.

Figure 6:
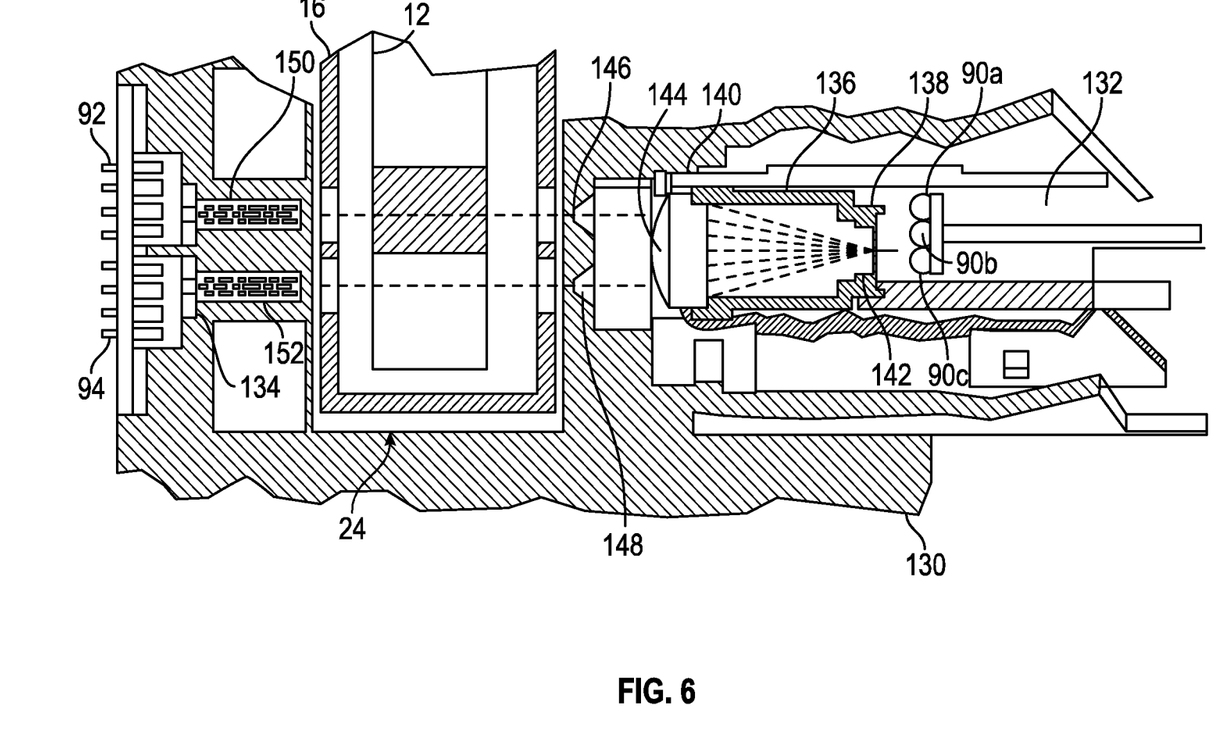
FIG. 6 is a partial cross-sectional view of a version of the measurement system of the analyzer showing exemplary locations of the light sources, cartridge holder, test cartridge and photodetectors within the analyzer.

Shown in FIG. 6 is a cross-sectional diagram of a portion of the measurement system 62 of the analyzer 10 containing the light sources 90, the sample photodetector 92, the reference photodetector 94, the test cartridge 12, and the cartridge holder 16. The measurement system 62 includes a support 130 defining a light source space 132, the test cartridge space 24, and a sample detector space 134. The test cartridge space 24 is positioned between the light source space 132 and the sample detector space 134. The support 130 is constructed so as to permit the light source space 132, the test cartridge space 24, and the sample detector space 134 to communicate so that light generated within the light source space 132 can pass through the test cartridge space 24 and be received within the sample detector space 134.

The measurement system 62 is provided with a lens and aperture holder 136 positioned in between the light source space 132 and the test cartridge space 24. In the example shown, three light sources 90a, 90b, and 90c are disposed within the light source space 132 and positioned so that light generated by the light sources 90a, 90b, and 90c is directed towards the test cartridge space 24 through the lens and aperture holder 136. The lens and aperture holder 136 has a first end 138 and a second end 140. The first end 138 is connected to a wall 142 in which an aperture (not shown) is disposed. The second end 140 supports a lens 144 designed to collimate light passing through the aperture. The support 130 includes a sample aperture 146 and a reference aperture 148 bordering the test cartridge space 24. When light is being generated by at least one of the light sources 90a, 90b and 90c, such light passes through the aperture within the wall 142, is collimated by the lens 144 and passes through the sample aperture 146 and the reference aperture 148. The light passing through the sample aperture 146 forms the sample beam 108, and the light passing through the reference aperture 148 forms the reference beam 110.

The sample photodetector 92, and the reference photodetector 94 are positioned within the sample detector space 134. The sample photodetector 92 is positioned to receive the sample beam 108, and the reference photodetector 94 is positioned to receive the reference beam 110. In one embodiment, collimating tubes 150 and 152 are positioned within the sample detector space 134 and adjacent to the test cartridge space 24. The collimating tube 150 is positioned in between the sample photodetector 92 and the test cartridge space 24 and serves to receive light from the test cartridge space 24 and transmit such light to the sample photodetector 92 in a collimated format. Likewise, the collimating tube 152 is positioned in between the reference photodetector 94 and the test cartridge space 24 and serves to receive light from the test cartridge space 24 and transmit such light to the reference photodetector 94 in a collimated format. As discussed above, in certain positions the cartridge holder 16 and the test cartridge 12 are positioned so as to pass light from the light source space 132 to the sample detector space 134; and in other positions the cartridge holder 16 and the test cartridge 12 are positioned so as to block light from passing from the light source space 132 to the sample detector space 134.

As will be appreciated by persons of ordinary skill in the art having the benefit of the instant disclosure, the light emitted by the light sources 90a, 90b and 90c may be processed, conditioned, filtered, diffused, polarized, or otherwise conditioned, prior to being detected by the sample photodetector 92 and/or the reference photodetector 94, for example. In one embodiment, the sample photodetector 92 and/or the reference photodetector 94 are photodiodes.

Further, in some embodiments of the inventive concepts disclosed herein, the light sources 90a, 90b and 90c may be supported within the light source space 132 in any desired manner, such as by being connected to the support 130 (e.g., via joints, seams, bolts, brackets, fasteners, welds, or combinations thereof), or by any other desired component of the analyzer 10.

As will be appreciated by persons skilled in the art, in some embodiments of the inventive concepts disclosed herein, more than three light sources 90a, 90b and 90c may be implemented, such as four, five or six light sources 90.

Figure 7:
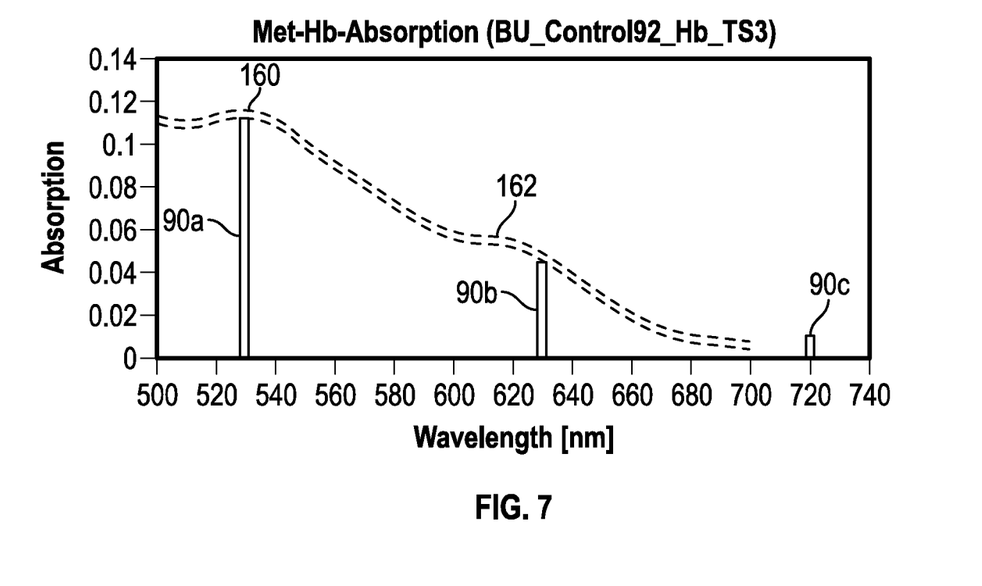
FIG. 7 is a graph showing an absorbance curve for a sample-hemoglobin reagent mixture designed to detect the presence of hemoglobin within the sample.
Figure 8:
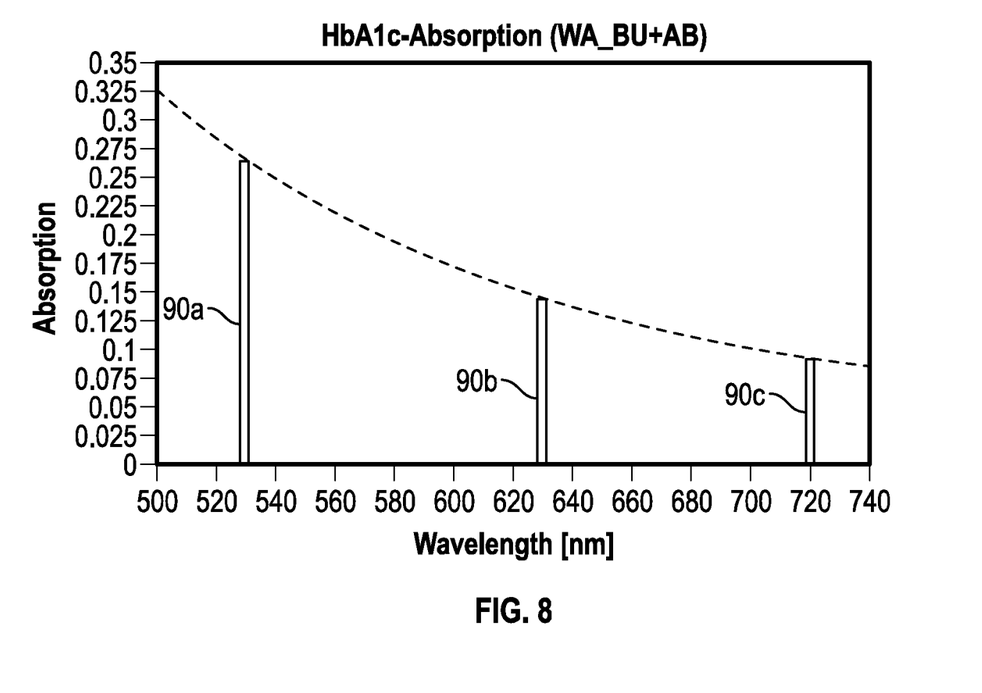
FIG. 8 is a graph showing an absorbance curve for a sample-hemoglobin A1c reagent mixture designed to detect the presence of hemoglobin A1c within the sample.

FIG. 7 is a graph showing an absorbance curve for a liquid test sample-hemoglobin reagent mixture designed to undergo an reaction and detect the presence of hemoglobin within the liquid test sample. As shown in FIG. 7, as the wavelength of light passing through the liquid test sample-hemoglobin mixture increases from 500 nm to 700 nm, the absorption of the light decreases and completely falls off at approximately 700 nm. FIG. 8 is a graph of an absorbance curve for a liquid test sample-hemoglobin A1c reagent mixture designed to detect the presence of a particular type of hemoglobin, i.e., A1c, within the liquid test sample. As shown in FIG. 8, as the wavelength of light passing through the liquid test sample-hemoglobin A1c reagent mixture undergoing an reaction increases from 500 nm to 750 nm, the absorption of the light decreases, yet remains well above zero.

In accordance with the presently disclosed inventive concepts, the measurement system 62 includes the plurality of the light sources 90a, 90b and 90c in which each of the light sources 90a, 90b and 90c emits light in a distinct range of wavelengths. In the example shown in FIGS. 7 and 8, the light source 90a emits light at a wavelength confined to a range from 480 nm to 580 nm, the light source 90b emits light at a wavelength confined to a range from 580 nm to 660 nm, and the light source 90c emits light at a wavelength confined to range from 660 nm to 780 nm. In one embodiment, the light source 90a emits light confined to a wavelength of approximately 531 nm corresponding to a first local peak 160 in the hemoglobin absorption curve depicted in FIG. 7; the light source 90b emits light confined to a wavelength of approximately 630 nm corresponding to a second local peak 162 in the hemoglobin absorption curve depicted in FIG. 7, and the light source 90c emits light confined to a wavelength of approximately 720 nm. The light emitted by the light source 90c is beyond the transmittance of the hemoglobin absorption curve depicted in FIG. 7, but within the hemoglobin A1c absorption curve depicted in FIG. 8 and when used to interrogate the test cartridge 12 supplies information with respect to the amount of hemoglobin A1c within the liquid test sample.

Figure 9:
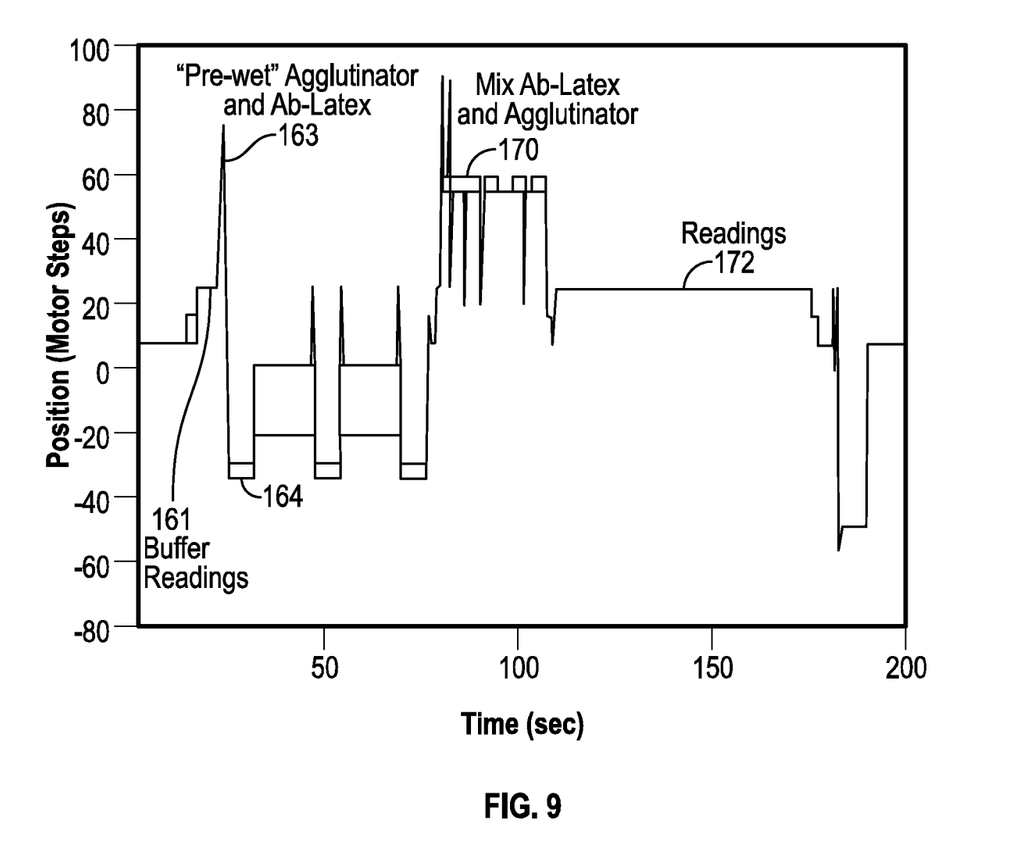
FIG. 9 is an exemplary graph showing an exemplary sequence of analyzing a liquid test sample undergoing an immunotype reaction for presence of multiple analytes of interest in accordance with the presently disclosed inventive concepts.

Shown in FIG. 9 is a time sequence chart showing an exemplary process for determining the presence of multiple analytes of interest within the liquid test sample. In the example shown, the liquid test sample is blood and a first analyte of interest is hemoglobin, and a second analyte of interest is hemoglobin A1c. The sequence descriptions contain 4 principal elements: time of the operation, e.g., in seconds relative to the start of the sequence, the operation (e.g. MOVE, READ), parameters that qualify the operation (where needed), and the rotational position of the test cartridge 12 in motor steps.

The "Time" column indicates the target time for each operation. Time 0 seconds in this column is approximately 5 seconds (non-critical) after the operator inserts the test cartridge 12 in the cartridge holder 16 and closes the optics door 22 to start the test. The target time for motor movements to move the cartridge holder 16 and/or mix the liquid test sample with one or more predetermined reagents is to be recorded at the start of the movement. Time stamps of READ operations are to be recorded at the completion of each READ operation.

Each READ operation typically takes multiple composite readings, e.g., 16 readings, of both the Liquid test sample and Reference A-to-D channels from the sample photodetector 92 and the reference photodetector 94 with each composite reading being composed of multiple individual sub-readings from a predetermined subset of the light sources 90a, 90b and 90c, e.g., with the light sources 90a, 90b and 90c within the predetermined subset enabled to generate light at separate and distinct instants of time. Each composite reading will include information obtained from enabling the light sources 90a, 90b, and 90c that are expected to obtain useful information from within the absorbance curve for the particular analyte of interest. Thus, when the measurement system 62 is determining the amount of hemoglobin within the liquid test sample, each composite reading will obtain and be calculated with a first transmittance value indicative of the transmittance of light from the light source 90a through the test cartridge 12, and also a second transmittance value of the transmittance of light from the light source 90b through the test cartridge 12. When the measurement system 62 is determining the amount of hemoglobin A1c within the liquid test sample, each composite reading will obtain and use a first transmittance value indicative of the transmittance of light from the light source 90a through the test cartridge 12, a second transmittance value of the transmittance of light from the light source 90b through the test cartridge 12, and a third transmittance value of the transmittance of light from the light source 90c through the test cartridge. The composite reading for determining hemoglobin or hemoglobin A1c will be a combination of the individual sub-readings, and the percentage hemoglobin A1c reading will be a ratio of the composite hemoglobin A1c reading/the composite hemoglobin reading. The sub-readings taken individually (e.g., one of the light sources 90a, 90b and 90c enabled to emit light at a time) and in sequence at separate instances of time with the light sources 90a, 90b and 90c can be combined into the composite reading using any suitable mathematical technique or algorithm, such as summing, averaging, differences or the like.

In this example, it should be noted that all motor movements are specified in full motor steps. In motor position Step 0, the top surface of the cartridge holder 16 may be parallel to the surface of the bench on which the analyzer 10 rests. Positive steps indicate test cartridge 12 rotation in the clockwise (CW) direction if one views the cartridge holder 16 from the side opposite from the source of motive force 98. When viewing the analyzer 10 from the front, steps in the positive direction rotate the test cartridge 12 toward the operator.

Entries in the Position column indicate the motor position at the end of the operation. A 200 step per revolution stepper motor is assumed. In this example, step +8 is the Home/Air read position (also the test cartridge load position). When a test cartridge 12 is loaded into the analyzer 10, the cartridge holder 16 is near the Home position, but the exact position may be verified at the start of each sequence because the operator may have rotated the cartridge holder 16 slightly while inserting the test cartridge 12. Step +16 is the Dark read position, and Step +25 is the Sample read position.

As a check that timing of the percentage HbA1c sequence does not deviate appreciably from the ideal timing, the actual time since the start of the measurement sequence may be checked against a continuously running hardware clock. If the difference between the ideal sequence time and the actual elapsed time exceeds +/−1.00 seconds, the analyzer 10 may post an error, rather than a reading of the liquid test sample.

Shown in FIG. 9 is an exemplary sequence for determining a percentage HbA1c/Hb reading. It should be understood, however, that the sequence can be modified to obtain other types of readings by the analyzer 10. As shown in FIG. 9, the sequence may begin by moving the cartridge holder 16 to the READ position and taking multiple composite readings of the transmittance/absorbance of the buffer solution at each of the distinct wavelength ranges by taking individual readings with each of the light sources 90a, 90b and 90c during a calibration stage 161. The composite readings of the buffer solution can be used as a baseline for all of the other measurements taken during the sequence. Then, the source of motive force 98 may be actuated in a clockwise direction to a pre-wetting stage 163 to pre-wet one or more particular reagents with the liquid test sample. In the example shown, for determining a relative percentage of Hb A1c to Hb, reagents known as an agglutinator and an Ab-latex are pre-wet with the liquid test sample, and then the source of motive force 98 is moved in a counter-clockwise direction to a first mixing stage 164 for mixing the liquid test sample with a particular reagent for determining the presence of Hb within the liquid test sample. Then, the source of motive force 98 is actuated to move the cartridge holder 16 and the test cartridge 12 into a second mixing stage 170 to mix the liquid test sample with the Hb A1c reagent, e.g., an antibody latex and agglutinator. As discussed above, the agglutinator (e.g., a synthetic polymer containing multiple copies of the immunoreactive portion of HbA1c) causes agglutination of latex coated with HbA1c specific mouse monoclonal antibody. This agglutination reaction causes increased scattering of light, which is measured as an increase in absorbance. Then, a reading stage 172 is entered and the cartridge holder 16 and the test cartridge 12 are again moved to the READ position and multiple composite readings relative to the buffer solution are taken and then averaged. Once the composite readings are taken of the amount of Hb A1c, and Hb, then the percentage of Hb A1c and Hb can be calculated and reported to the user using the user interface 34.

During the reading stage 172, multiple, e.g., ten, composite measurements of the amount of Hb and HbA1c may be simultaneously taken. Each composite measurement may include 3 A-to-D readings (one for each light source 90a, 90b, or 90c) on each channel of the sample photodetector 92 and the reference photodetector 94 (six total readings per composite measurement). The readings may be paired and alternated in time, i.e. a single reading of the sample beam 108 by the sample photodetector 92 followed by a single reading of the reference beam 110 by the reference photodetector 94. (The order or the readings does not matter; either sample beam 108 or reference beam 110 may be read first as long as the individual readings are alternated.) All 60 readings (30 sample beam 108 measurements and 30 reference beam 110 measurements) for 10 composite measurements should be completed within approximately 6 seconds, e.g., 30 milliseconds per reading. The mean, standard deviation (SD) and percent coefficient of variation (% CV) may be computed for each set of 10 readings, for example. This same procedure can be followed to obtain any desired number of readings.

In the analyzer 10, the simultaneous readings are taken by individually and sequentially (1) enabling the light sources 90a, 90b and 90c to generate light for an amount of time, and (2) taking a reading. It should be noted that in some embodiments, readings are not taken when two or more of the light sources 90a, 90b and 90c are enabled to generate light simultaneously due to the occurrence of unwanted interference. Once the readings are taken, the calibration parameters and an algorithm for solving simultaneous equations can be used to determine an amount of at least two analytes of interest, e.g., Hb and HbA1c, simultaneously within the liquid test sample-reagent mixture.

In one embodiment, both Hb and HbA1c can be determined simultaneously by setting up a Beer-Lambert equation ($A=C*E$) as a matrix equation (a set of simultaneous equations) and solving for the concentrations of Hb and HbA1c at once without having to isolate the measurement of Hb. With 3 wavelengths, C can be the concentrations of Hb, HbA1c, and 1 interfering substance. E can be a 2×3 matrix of the calibration parameters that may be determined by running a series of experiments with a sample reagent mixture having known concentrations of the analytes of interest. A can be a 3×1 matrix of the readings taken by the analyzer 10. The set of simultaneous equations can be solved using any suitable algorithm, such as an interative technique such as a Newton method, a bisection method, or a secant method. Other methods of solving simultaneous equations can also be used.

Measured voltages by the sample photodetector 92 and by the reference photodetector 94 represent light measured in motor position step +8 (Air read position) or motor position step +25 (Sample read position) for the sample and reference beams 108 and 110 respectively. Offset voltages for each channel may also be obtained with the optical paths blocked (e.g., motor position step +16). All of the measurements may be taken at the same fixed gain value.

To minimize the interval for lamp drift, the buffer readings may be referenced to the air (100% transmittance) and dark readings (0% transmittance). In a similar manner, the hemoglobin readings may be referenced to the air readings. For example, the hemoglobin and hemoglobin A1c readings during the reading stage 172 are referenced to the air reading.

The methods and systems described herein are not limited to a particular hardware or software configuration, and may find applicability in many computing or processing environments. The methods and systems may be implemented in hardware or software, or a combination of hardware and software. The methods and systems may be implemented in one or more computer programs, where a computer program may be understood to include one or more processor executable instructions.

The main processor 68 may be implemented as a computer system including a single processor or multiple processors working together or independently to execute the processor executable instructions described below. Embodiments of the main processor 68 may include a digital signal processor (DSP), a central processing unit (CPU), a microprocessor, a multi-core processor, an application specific integrated circuit, and combinations thereof. The main processor 68 may be coupled to the processor-readable memory 69. The non-transitory processor-readable memory 69 may be implemented as RAM, ROM, flash memory, or the like, as described in more detail below. The processor-readable memory 69 may be a single non-transitory processor-readable memory, or multiple non-transitory processor-readable memories functioning logically together or independently.

References herein to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

References to the processor-readable memory 69, unless otherwise specified, may include one or more processor-readable and accessible non-transitory computer readable medium and/or components that may be internal to the main processor 68, external to the main processor 68, and/or may be accessed via a wired or wireless network using a variety of communications protocols, and unless otherwise specified, may be arranged to include a combination of external and internal memory devices, where such memory may be contiguous and/or partitioned based on the application and where such memory may be non-transitory in nature. The non-transitory computer readable medium may be implemented as RAM, a hard drive, a hard drive array, a solid state drive, a flash drive, a memory card, or the like, as well as combinations thereof. When more than one non-transitory computer readable medium is used, one of the non-transitory computer readable medium may be located in the same physical location as the main processor 68, and another one of the non-transitory processor-readable mediums may be located in a location remote from the main processor 68. The physical location of the non-transitory computer readable medium may be varied and the non-transitory computer readable medium may be implemented as a "cloud memory," i.e. non-transitory computer readable medium which is partially or completely based on or accessed using a network which may be accessed by the main processor 68 using the network interface 60.

The main processor 68 may execute processor executable instructions, also referred to herein as computer program(s) to perform the logic described herein. References herein to microprocessor instructions, microprocessor-executable instructions, processor executable instructions, or computer program(s), in accordance with the above, may be understood to include programmable hardware. The computer program(s) may be implemented using one or more high level procedural or object-oriented programming languages to communicate with a computer system; however, the program(s) may be implemented in assembly or machine language, if desired. The language may be compiled or interpreted.

As provided herein, in one embodiment, the analyzer 10 may operate independently or with other devices in a networked environment. References to a network, unless provided otherwise, may include one or more intranets and/or the internet. The network may permit bi-directional communication of information and/or data between the main processor 68, and another computer system located external to the housing 20 using the network interface 60. The network may include, for example, a Local Area Network (LAN), wide area network (WAN), and/or may include an intranet and/or the internet and/or another network. The network(s) may be wired or wireless or a combination thereof and may use one or more communications protocols and a plurality of network topographies to facilitate communications. Accordingly, the methods and systems may utilize multiple processors and/or processor devices, and the processor instructions may be divided amongst such single- or multiple-processor/devices.

While the present invention has been described in connection with the exemplary embodiments of the various figures, it is not limited thereto and it is to be understood that other similar embodiments may be used or modifications and additions may be made to the described embodiments for performing the same function of the present invention without deviating therefrom. Therefore, the present invention should not be limited to any single embodiment, but rather should be construed in breadth and scope in accordance with the appended claims. Also, the appended claims should be construed to include other variants and embodiments of the invention, which may be made by those skilled in the art without departing from the true spirit and scope of the present invention.

What is claimed is:

1. An analyzer, comprising:
a housing surrounding space sized and configured to receive a test cartridge;
a test cartridge within the test cartridge space, the test cartridge containing-reagents mixture, contained with the test cartridge and configured to undergo an immunotype reaction, the liquid test sample-reagents mixture having a plurality of reagents;
a first light source generating a first beam of light passing through the test cartridge space, the first beam of light having a first wavelength range;
a second light source generating a second beam of light passing through the test cartridge space, the second beam of light having a second wavelength range different from the first wavelength range;
a third light source generating a third beam of light passing through the test cartridge space, the third beam of light having a third wavelength range different from the first and second wavelength range;
at least one sample detector positioned to receive one or more of the first, second and third beams of light subsequent to the first, second and third beams of light passing through the test cartridge space to generate first, second and third signals, wherein the first, second and third signals are absorption readings;
a computer system having a processor with a non-transitory computer readable medium storing a set of computer executable instructions for running on a processor that when executed cause the processor to:
receive the first, second, and third signal indicative of absorption readings captured by the sample detector at first, second and third instants of time from the first, second and third light sources and to use the first, second, and third signals indicative of absorption readings with calibration data to simultaneously determine an amount of a first analyte and a second analyte simultaneously present within the liquid test sample reagents mixture; and a cartridge holder configured to mate with and support the test cartridge; the cartridge holder configured to rotate between a first position wherein the cartridge holder and the test cartridge are positioned to pass light from the first light source and the second light source to the sample detector, and a second position wherein the cartridge holder and the test cartridge are positioned to block light from the first light source and the second light source to the sample detector.

2. The analyzer of claim 1, wherein the first wavelength range is from 580 nm to 660 nm.

3. The analyzer of claim 1, wherein the second wavelength range is from 660 nm to 790 nm.

4. The analyzer of claim 1, wherein the second wavelength range is from 700 nm to 740 nm.

5. The analyzer of claim 1, wherein the third wavelength range is from 480 nm to 580 nm.

6. The analyzer of claim 1, wherein the first light source, the second light source and the third light source is a single light source having the ability to generate and output the first, second and third beams of light.

7. The analyzer of claim 6, wherein the single light source generates mixed wavelength light, and further includes a separator configured to receive the mixed wavelength light and separate the mixed wavelength light into the first, second and third wavelength ranges.

8. The analyzer of claim 1, wherein the first light source, the second light source and the third light source are separate.

9. The analyzer of claim 1, wherein the cartridge holder includes a home air read aperture, a reference air read aperture and a sample read aperture with each of the home air read aperture, reference air read aperture and sample read aperture configured to selectively pass or block light.

10. The analyzer of claim 9, wherein the light emitted by the light sources are split into a sample beam configured to pass through the test cartridge and a reference beam configured to avoid the test cartridge wherein the light of the sample beam is received by the at least one sample detector and the light of the reference beam is received by a reference photodetector and converted into a reference signal indicative of transmittance of light outside of the test cartridge.

11. The analyzer of claim 10, wherein the cartridge holder has an air read position configured to pass the sample beam through the home air read aperture and pass the reference beam through the home air read aperture.

12. The analyzer of claim 11, wherein the cartridge holder has a sample read position configured to pass the sample beam through the sample read aperture and the reference beam through the reference air read aperture.

13. The analyzer of claim 12, wherein the cartridge holder has a dark read position configured to block the sample beam and the reference beam.

14. The analyzer of claim 1, wherein the first analyte is hemoglobin and the second analyte is glycated hemoglobin (HbA1c).

15. The analyzer of claim 1, wherein the plurality of reagents includes an agglutinator.

* * * * *

UNITED STATES PATENT AND TRADEMARK OFFICE
CERTIFICATE OF CORRECTION

PATENT NO. : 11,668,707 B2
APPLICATION NO. : 16/468963
DATED : June 6, 2023
INVENTOR(S) : Jacques Brunelle It is certified that error appears in the above-identified patent and that said Letters Patent is hereby corrected as shown below:

In the Claims

Column 17, Line 25, in Claim 1, after the wording "a housing surrounding", insert --a test cartridge--.

Column 17, Lines 25-26, in Claim 1, delete the wording "sized and configured to receive a test cartridge".

Column 17, Lines 27-28, in Claim 1, after the wording "the test cartridge containing", insert --a liquid test sample--.

Signed and Sealed this
Twenty-ninth Day of August, 2023

*Katherine Kelly Vidal*
Katherine Kelly Vidal
*Director of the United States Patent and Trademark Office*